United States Patent [19]

Matsuda et al.

[11] Patent Number: 5,894,073
[45] Date of Patent: Apr. 13, 1999

[54] PROCESS FOR THE PREPARATION OF 2-CHLORO-5-CHLOROMETHYL-1,3-THIAZOLE

[75] Inventors: Hideki Matsuda; Goro Asanuma; Manzo Shiono, all of Kurashiki, Japan

[73] Assignee: Kuraray Co., Ltd., Kurashiki, Japan

[21] Appl. No.: 08/804,401

[22] Filed: Feb. 21, 1997

[30] Foreign Application Priority Data

| Feb. 21, 1996 | [JP] | Japan | 8-033649 |
| May 23, 1996 | [JP] | Japan | 8-128694 |
| May 23, 1996 | [JP] | Japan | 8-128695 |
| May 24, 1996 | [JP] | Japan | 8-129781 |
| Aug. 5, 1996 | [JP] | Japan | 8-205885 |
| Aug. 6, 1996 | [JP] | Japan | 8-207045 |
| Aug. 6, 1996 | [JP] | Japan | 8-207046 |

[51] Int. Cl.$^6$ ............... C07C 331/04; C07D 277/32
[52] U.S. Cl. ............... 548/202; 558/15; 558/19
[58] Field of Search ............... 558/19; 548/202

[56] References Cited

U.S. PATENT DOCUMENTS

5,705,652  1/1998  Jackson ............... 548/202

FOREIGN PATENT DOCUMENTS

| 0 260 560 | 9/1987 | European Pat. Off. . |
| 0 446 913 | 3/1991 | European Pat. Off. . |
| 0 763 531 | 3/1997 | European Pat. Off. . |
| 63-83079 | 4/1988 | Japan . |
| 4-234864 | 8/1992 | Japan . |
| 6-776 | 1/1994 | Japan . |

OTHER PUBLICATIONS

Journal f. prakt. Chemie, vol. 322, No. 4, pp. 629–637, 1980, K. Schulze, et al., "Zur Darstellung Und Charakterisierung Von Vinylsenfölen".

*Primary Examiner*—Robert Gerstl
*Attorney, Agent, or Firm*—Oblon, Spivak, McClelland, Maier & Neustadt, P.C.

[57] ABSTRACT

According to the present invention, provided are (1) a process for the preparation of 2-chloro-5-chloromethyl-1,3-thiazole, by reacting 3-chloro-1-isothiocyanato-1-propene with a chlorinating agent, (2) a process for the preparation of 3-chloro-1-isocyanato-1-propene, by rearranging 3-chloro-1-thiocyanato-2-propene in the presence of a salt of one or more than one metal selected from the group consisting of metals belonging to Group 2A, Group 7A, Group 8 and Group 1B of the long-form periodic table, and (3) a process for the preparation of 3-chloro-1-thiocyanato-2-propene, by reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst.

32 Claims, No Drawings

PROCESS FOR THE PREPARATION OF 2-CHLORO-5-CHLOROMETHYL-1,3-THIAZOLE

BACKGROUND OF THE INVENTION

1. Field of the Invention

This invention relates to a process for the preparation of 2-chloro-5-chloromethyl-1,3-thiazole. 2-Chloro-5-chloromethyl-1,3-thiazole prepared according to the present invention is useful as a synthesis intermediate for agricultural chemicals, for example, as a synthesis intermediate for hexahydrotriazine compounds useful as insecticides (refer to Japanese Patent Publication No. HEI 6-776).

2. Discussion of the Background

As a preparation process of 2-chloro-5-chloromethyl-1,3-thiazole, known are (1) a process of reacting allyl isothiocyanate with chlorine (refer to Japanese Patent Application Laid-Open No. SHO 63-83079) and (2) a process of reacting 2-chloroallyl isothiocyanate with a chlorinating agent (refer to Japanese Patent Application Laid-Open No. HEI 4-234864).

The reaction described in the above process (1) is however markedly severe reaction which requires a large excess amount of a chlorinating agent and high temperature and in addition, plural byproducts are formed together with the target product 2-chloro-5-chloromethyl-1,3-thiazole so that this process is accompanied by the problem that 2-chloro-5-chloromethyl-1,3-thiazole so obtained has low purity. On the other hand, the process described in the above (2) is also accompanied with the problem that 2-chloroallyl isothiocyanate, which is a starting material, is not available at low cost. Accordingly, it is difficult to say that each of these processes is an industrially excellent process for the preparation of 2-chloro-5-chloromethyl-1,3-thiazole.

In addition, a process of heating 3-chloro-1-thiocyanato-2-propene in dioxane is known as a process for the preparation of 3-chloro-1-isothiocyanato-1-propene (refer to Journal f. prakt. Chemie. 322(4), 629(1980)).

It is however known that the above process has a low yield (refer to Comparative Example 2 which will be described below) and dioxane which is used as a solvent is carcinogenic. Accordingly, it is difficult to say that this process is industrially advantageous for the preparation of 3-chloro-1-isothiocyanato-1-propene.

Furthermore, as a process for the preparation of 3-chloro-1-thiocyanato-2-propene, a process of reacting 1,3-dichloropropene and potassium thiocyanate in dimethyl sulfoxide is shown (refer to Journal f. prakt. Chemie. 322(4), 629(1980)).

The above process however has a yield as low as 47% so that it is difficult to say that it is an industrially advantageous process for the preparation of 3-chloro-1-thiocyanato-2-propene.

With respect to the processes described in the above (1) and (2), isolation and purification of 2-chloro-5-chloromethyl-1,3-thiazole are carried out by distillation.

Since 2-chloro-5-chloromethyl-1,3-thiazole has low thermal stability and its reflux ratio cannot be increased, 2-chloro-5-chloromethyl-1,3-thiazole purified by distillation has a low purity. It is difficult to say that distillation is an excellent purification method for 2-chloro-5-chloromethyl-1,3-thiazole. Accordingly, there is a demand for a purification method to obtain 2-chloro-5-chloromethyl-1,3-thiazole having a higher purity.

SUMMARY OF THE INVENTION

An object of the present invention is to provide an industrially advantageous process for preparing 2-chloro-5-chloromethyl-1,3-thiazole under mild conditions using an easily available and inexpensive starting material without using a large excess amount of a chlorinating agent.

Another object of the present invention is to provide an industrially advantageous process for the preparation of 3-chloro-1-isothiocyanato-1-propene in high purity and in high yield.

A further object of the present invention is to provide an industrially advantageous process for the preparation of 3-chloro-1-thiocyanato-2-propene in high purity and in high yield.

A still further object of the present invention is to provide a process for the purification of 2-chloro-5-chloromethyl-1,3-thiazole with good purity.

In a first aspect of the present invention, there is thus provided a process for the preparation of 2-chloro-5-chloromethyl-1,3-thiazole, which comprises reacting 3-chloro-1-isothiocyanato-1-propene with a chlorinating agent.

In a second aspect of the present invention, there is also provided a process for the preparation of 2-chloro-5-chloromethyl-1,3-thiazole, which comprises rearranging 3-chloro-1-thiocyanato-2-propene in the presence of a salt of one or more than one metal selected from the group consisting of metals belonging to Group 2A, Group 7A, Group 8 and Group 1B of the long-form periodic table to obtain 3-chloro-1-isothiocyanato-1-propene; and reacting the 3-chloro-1-isothiocyanato-1-propene with a chlorinating agent.

In a third aspect of the present invention, there is also provided a process for the preparation of 3-chloro-1-isothiocyanato-1-propene, which comprises rearranging 3-chloro-1-thiocyanato-2-propene in the presence of a salt of one or more than one metal selected from the group consisting of metals belonging to Group 2A, Group 7A, Group 8 and Group 1B of the long-form periodic table.

In a fourth aspect of the present invention, there is also provided a process for the preparation of 2-chloro-5-chloromethyl-1,3-thiazole, which comprises reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst, to obtain 3-chloro-1-thiocyanato-2-propene; rearranging the 3-chloro-1-thiocyanato-2-propene in the presence of a salt of one or more than one metal selected from the group consisting of metals belonging to Group 2A, Group 7A, Group 8 and Group 1B of the long-form periodic table to obtain 3-chloro-1-isothiocyanato-1-propene; and reacting the 3-chloro-1-isothiocyanato-1-propene with a chlorinating agent.

In a fifth aspect of the present invention, there is also provided a process for the preparation of 3-chloro-1-isothiocyanato-1-propene, which comprises reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst, to obtain 3-chloro-1-thiocyanato-2-propene; and rearranging the 3-chloro-1-thiocyanato-2-propene in the presence of a salt of one or more than one metal selected from the group consisting of metals belonging to Group 2A, Group 7A, Group 8 and Group 1B of the long-form periodic table.

In a sixth aspect of the present invention, there is also provided a process for the preparation of 3-chloro-1-thiocyanato-2-propene, which comprises reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst.

In a seventh aspect of the present invention, there is also provided a process for the purification of 2-chloro-5-chloromethyl-1,3-thiazole, which comprises recrystallizing crude 2-chloro-5-chloromethyl-1,3-thiazole using one or more than one organic solvent selected from the group consisting of hydrocarbons, ethers, aldehydes, ketones, esters and alcohols.

DETAILED DESCRIPTION OF THE PREFERRED EMBODIMENTS

Each of the preparation processes of the present invention will hereinafter be described specifically.

Process 1

A process to obtain 3-chloro-1-thiocyanato-2-propene by reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst:

Examples of the thiocyanate salts include alkali metal salts such as sodium thiocyanate and potassium thiocyanate; alkaline earth metal salts such as calcium thiocyanate and magnesium thiocyanate; and ammonium thiocyanate. Among them, sodium thiocyanate is preferred. It is desired that the thiocyanate is used in an amount of 1.0 to 1.5 moles per mole of 1,3-dichloropropene.

Process 1-(a)

In the case where 1,3-dichloropropene and a thiocyanate salt are reacted in the presence of water:

It is preferred that the amount of water which is allowed to exist in the reaction system is 0.5 to 10 times the weight of 1,3-dichloropropene, with 0.5 to 2.0 times being more preferred.

The reaction can be performed in the presence of a phase transfer catalyst. Examples of the catalyst include quaternary ammonium salts and quaternary phosphonium salts. Among them, tetraalkylammonium halides such as tetramethylammonium chloride, benzyltrimethylammonium chloride and tetrabutylammonium chloride are preferred. It is desired that the phase transfer catalyst is used in an amount of 0.001 to 0.01 mole per mole of 1,3-dichloropropene.

The reaction can be performed either in the presence of a solvent or in a solventless manner. No particular limitation is imposed on the solvent insofar as it does not adversely affect the reaction. Examples include hydrocarbons such as benzene, toluene, hexane, heptane and octane; halogenated hydrocarbons such as dichloromethane, chloroform, carbon tetrachloride, 1,2-dichloroethane and 1,1,2,2-tetrachloroethane; and ethers such as diethyl ether, diisopropyl ether and dimethoxyethane. It is preferred that the solvent is used in an amount of 0.5 to 10 times the weight of 1,3-dichloropropene, with 1.0 to 2.0 times being more preferred.

The preferred reaction temperature falls within a range of from 0° C. to 150° C., with 20° C. to 80° C. being more preferred. The reaction time differs depending on the reaction conditions, however, 1 to 4 hours are generally suitable.

Process 1-(b)

In the case where 1,3-dichloropropene and a thiocyanate salt are reacted in the presence of an organic solvent which is water-soluble and has a boiling point of 150° C. or lower:

In the case where an organic solvent which is not water-soluble is used singly, 3-chloro-1-thiocyanato-2-propene cannot be obtained in a high yield (refer to Comparative Example I which will be described below). In addition, when an organic solvent which has a boiling point higher than 150° C., for example, dimethyl sulfoxide (having a boiling point of about 160° C.) is used singly, the yield of the target product is as low as 47% (refer to Journal f. prakt. Chemie. 322(4), 629(1980)).

Examples of the organic solvent which is water-soluble and has a boiling point of 150° C. or lower include nitriles such as acetonitrile and propionitrile; alcohols such as methanol, ethanol and propanol; and ketones such as acetone. These solvents may be used in combination. It is more preferred that the boiling point of the solvent is 100° C. or lower. It is preferred that the solvent is used in an amount of 0.5 to 10 times the weight of the thiocyanate salt, with 1.0 to 2.0 times being more preferred.

The reaction temperature preferably ranges from 0° C. to 150° C., with 20° C. to 80° C. being more preferred. The reaction time differs depending on the reaction conditions, however, the reaction time of 1 to 4 hours is generally suitable.

Process 1-(c)

In the case where 1,3-dichloropropene and a thiocyanate salt are reacted in an organic solvent in the presence of a phase transfer catalyst:

No particular limitation is imposed on the organic solvent usable in the present invention insofar as it does not adversely affects the reaction. Examples include hydrocarbons such as benzene, toluene, hexane, heptane and octane; halogenated hydrocarbons such as dichloromethane, chloroform, carbon tetrachloride, 1,2-dichloroethane and 1,1,2,2-tetrachloroethane; ethers such as diethyl ether, diisopropyl ether, dimethoxyethane and tetrahydrofuran; ketones such as acetone, methyl ethyl ketone and cyclohexanone; nitriles such as acetonitrile and propionitrile; alcohols such as methanol, ethanol and propanol; and dimethyl sulfoxide. It is preferred that the organic solvent is used in an amount of 0.5 to 10 times the weight of the thiocyanate salt, with 1.0 to 2.0 times being more preferred. Alternatively, it is also possible to use 1,3-dichloropropene, which is a reaction substrate, in an excess amount in order to let it serve as a solvent in addition.

Such a reaction is carried out in the presence of a phase transfer catalyst. The use of the phase transfer catalyst makes it possible to prepare 3-chloro-1-thiocyanato-2-propene in high yield. For example, in the case where dimethyl sulfoxide is used as a solvent, if the phase transfer catalyst is not employed, the yield is 47%, while it rises even to 70% by the use of the phase transfer catalyst (refer to Journal f. prakt. Chemie. 322(4), 629(1980) and also Example 8 which will be described below). When diisopropyl ether is used as a solvent, reaction hardly proceeds without the use of the phase transfer catalyst, but the yield rises even to 82% by the use of the phase transfer catalyst (refer to Example 6 and Comparative Example 1 which will be described below).

Examples of the phase transfer catalyst include quaternary ammonium salts and quaternary phosphonium salts. Among them, tetramethylammonium chloride, tetraethylammonium chloride, tetrabutylammonium chloride and benzyltrimethylanunonium chloride are preferred. It is generally suitable that the phase transfer catalyst is used in an amount of 0.001 to 0.01 mole per mole of 1,3-dichloropropene.

The reaction temperature preferably falls within a range of from 0° C. to 150° C., with a range of from 20° C. to 80° C. being more preferred. The reaction time differs depending on the reaction conditions but that of 1 to 4 hours is generally suitable.

The isolation and purification of 3-chloro-1-thiocyanato-2-propene from the reaction mixture are effected in a manner known per se in the art. For example, after being cooled, the reaction mixture is extracted with an organic solvent such as toluene, diethyl ether, methylene chloride, ethyl acetate or the like. The extract is then washed with saturated saline, dried and concentrated under reduced pressure. The resulting concentrate is then isolated and purified by distillation under reduced pressure or chromatography or similar means. Alternatively, 3-chloro-1-thiocyanato-2-propene can be provided for the subsequent reaction without being isolated and purified from the reaction mixture.

Incidentally, 1,3-dichloropropene which is employed as a starting material is mass produced as an insecticide so that it is easily available at a low cost.

Process 2

A process to obtain 3-chloro-1-isothiocyanato-1-propene by rearranging 3-chloro-1-thiocyanato-2-propene in the presence of a salt of one or more than one metal selected from the group consisting of metals belonging to Group 2A, Group 7A, Group 8 and Group 1B of a long-form periodic table:

Examples of the metal salt usable in such a reaction include salts of a metal belonging to Group 2A, Group 7A, Group 8 or Group 1B of a long-form periodic table. Examples of the metal belonging to Group 2A include magnesium, calcium and barium; those of the metal belonging to Group 7A include manganese; those of the metal belonging to Group 8 include iron, ruthenium, cobalt, rhodium, nickel, palladium and platinum; and those of the metal belonging to Group 1B include copper, silver and gold.

These metals are used in the form of a metal salt. Examples of the metal salt include halides such as chloride, bromide and iodide; inorganic salts such as sulfate, nitrate, phosphate, hydroxide, carbonate and thiocyanate; organic salts such as acetate, benzoate and acetylacetonate; and oxides.

Specific examples of the metal salt include magnesium salts such as magnesium chloride, magnesium bromide, magnesium sulfate, magnesium oxide and magnesium acetate; manganese salts such as manganese chloride; iron salts such as ferrous (or ferric) sulfate and ferrous (or ferric) nitrate; ruthenium salts such as ruthenium chloride; cobalt salts such as cobalt chloride, cobalt bromide, cobalt sulfate and cobalt acetate; nickel salts such as nickel chloride and nickel bromide; palladium salts such as palladium chloride and palladium acetate; and copper salts such as copper (I) chloride, copper (II) chloride, copper sulfate, copper thiocyanate, copper (I) oxide, copper (II) oxide, copper acetate and copper acetylacetonate. A better yield can be obtained when magnesium chloride, cobalt chloride or copper (II) chloride is used among the above-exemplified metal salts. These metal salts can be used either singly or in combination.

It is preferred that the metal salt is used in an amount falling within a range of from 0.01 to 0.1 mole per mole of 3-chloro-1-thiocyanato-2-propene.

Such a reaction can be carried out either in the presence of a solvent or in a solventless manner. No particular limitation is imposed on the solvent to be employed insofar as it does not adversely affect the reaction. Examples include hydrocarbons such as toluene, xylene, hexane, heptane and octane; halogenated hydrocarbons such as dichloromethane, chloroform, carbon tetrachloride, 1,2-dichloroethane and 1,1,2,2-tetrachloroethane; ethers such as diethyl ether, diisopropyl ether and dimethoxyethane; nitriles such as acetonitrile and propionitrile; and amides such as dimethyl formamide. It is preferred that the solvent is used in an amount of 1 to 50 times the weight of 3-chloro-1-thiocyanato-2-propene, with 4 to 20 times being more preferred.

The reaction temperature preferably falls within a range of from 0° C. to 200° C., with a range of from 100° C. to 150° C. being more preferred. The reaction time differs depending on the reaction conditions but that of 0.5 to 5 hours is generally suitable.

The isolation and purification of 3-chloro-1-isothiocyanato-1-propene from the resulting reaction mixture are carried out in a manner known per se in the art.

Described specifically, after cooling the reaction mixture, the metal salt is removed therefrom by filtration. The filtrate is then concentrated under reduced pressure. The resulting concentrate is then isolated and purified by distillation under reduced pressure or chromatography or the like means. Alternatively, 3-chloro-1-isothiocyanato-1-propene can be provided for the subsequent reaction without isolation and purification from the reaction mixture.

Process 3

A process to obtain 2-chloro-5-chloromethyl-1,3-thiazole by reacting 3-chloro-1-isothiocyanato-1-propene with a chlorinating agent:

Such a reaction can be carried out either in the presence of a solvent or in a solventless manner. No particular limitation is imposed on the solvent to be employed insofar as it does not adversely affect the reaction. Examples include halogenated hydrocarbons such as dichloromethane, chloroform, carbon tetrachloride, 1,2-dichloroethane and 1,1,2,2-tetrachloroethane; hydrocarbons such as benzene, toluene, hexane, heptane and octane; ethers such as diethyl ether, diisopropyl ether, tetrahydrofuran, dioxane and dimethoxyethane; nitriles such as acetonitrile and propionitrile; amides such as dimethylformamide; and dimethyl sulfoxide. It is preferred that the solvent is used in an amount of 0.5 to 10 times the weight of 3-chloro-1-isothiocyanato-1-propene, with 0.5 to 2.0 times being more preferred.

As the chlorinating agent to be employed for the reaction, chlorine or a compound which emits chlorine under the reaction conditions, for example, sulfuryl chloride can be used. From the viewpoint of the yield, sulfuryl chloride is preferred. It is preferred that the chlorinating agent is used generally in an amount falling within a range of from 1.0 equivalent to 1.5 equivalents relative to 3-chloro-1isothiocyanato-1-propene. In the case where chlorine is used as the chlorinating agent, on the other hand, it is possible to introduce a chlorine gas directly into the reaction system or to use chlorine dissolved in a solvent. As such a solvent, the above-exemplified ones can be used.

The reaction temperature preferably falls within a range of from −20° C. to 150° C., with a range of from 0° C. to 60° C. being more preferred. The reaction time differs depending on the reaction conditions but that of 1 to 4 hours is generally suitable.

In Process 3, it is preferred to use trans-3-chloro-1-isothiocyanato-1-propene as a starting material since use of this compound makes it possible to provide the target compound in a high yield. Trans-3-chloro-1-isothiocyanato-1-propene can be obtained by distilling and separating 3-chloro-1-isothiocyanato-1-propene which is a mixture of a cis-form and a trans-form. The cis-form separated here can be converted into the trans-form by isomerization. Alternatively, it is possible to use a mixture of the cis-form and trans-form of 3-chloro-1-isothiocyanato-1-propene as the starting material without isolating the trans-form in advance and to carry out the reaction of the present invention while isomerizing the cis-form into the trans-form. The cis-form can be isomerized into the trans-form in the presence of a catalyst generally used for the isomerization of a double bond. Examples of such a catalyst include iodine; thiols such as thiophenol; and Lewis acids.

Incidentally, the use of magnesium chloride as a metal salt in the reaction of Process 2 makes it possible to provide trans-rich 3-chloro-1-isothiocyanato-1-propene and is therefore preferred.

The isolation and purification of 2-chloro-5-chloromethyl-1,3-thiazole from the reaction mixture so obtained are carried out in a manner known per se in the art. Described specifically, after being cooled, the reaction mixture is poured in an alkaline aqueous solution such as sodium bicarbonate, sodium carbonate or sodium hydroxide. The resulting mixture is extracted with chloroform or the like. The extract is washed with water, dried and then concentrated under reduced pressure. The concentrate is then isolated and purified by chromatography or similar means.

Process 4

A process of recrystallizing crude 2-chloro-5-chloromethyl-1,3-thiazole using one or more than one organic solvent selected from the group consisting of hydrocarbons, ethers, aldehydes, ketones, esters and alcohols:

A description will next be made of the organic solvent used for such a purification process. Examples of the hydrocarbons include aliphatic hydrocarbons such as pentane, hexane, heptane and octane; aromatic hydrocarbons such as benzene, toluene and xylene; and halogenated hydrocarbons such as methylene chloride, chloroform and carbon tetrachloride. Examples of the ethers include diethyl ether, diisopropyl ether and 1,2-dimethoxyethane. Examples of the aldehydes include propionaldehyde and isobutyl aldehyde. Examples of the ketones include acetone, methyl ethyl ketone and methyl isobutyl ketone. Examples of the esters include ethyl acetate and butyl acetate. Examples of the alcohols include methanol, ethanol, propanol and butanol. It is preferred that the solvent is used in an amount of 0.5 to 20 times the weight of the crude 2-chloro-5-chloromethyl-1,3-thiazole, with 1 to 5 times being more preferred.

The crystallization temperature preferably falls within a range of $-50°$ C. to $30°$ C., with a range of $-30°$ C. to $0°$ C. being more preferred.

No particular limitation is imposed on the preparation process of the crude 2-chloro-5-chloromethyl-1,3-thiazole usable in the present invention. Examples of the preparation process of the crude 2-chloro-5-chloromethyl-1,3-thiazole include a process of the present invention, a process of reacting allyl isothiocyanate with chlorine (refer to Japanese Patent Application Laid-Open No. SHO 63-83079) and a process of reacting 2-chloroallyl isothiocyanate with a chlorinating agent (refer to Japanese Patent Application Laid-Open No. HEI 4-234864).

The reaction concentrate, distillate or the like so obtained can be provided for the purification process of the present invention.

EXAMPLES

The present invention will hereinafter be described more specifically by examples. It should however be borne in mind that the present invention is not limited to or by the following examples. Percentages are given in weight percent.

PROCESS 1

Example 1

In 250 ml of water, 200 g of sodium thiocyanate were dissolved. To the resulting solution, 250 g of 1,3-dichloropropene and 2.5 g of tetrabutylammonium chloride were added, followed by heating at $60°$ C. for 3 hours. The reaction mixture was cooled down to room temperature and poured in 200 ml of water, followed by extraction with 500 ml of xylene once. The organic layer was washed with 500 ml of saturated saline, dried over anhydrous sodium sulfate and then concentrated under reduced pressure. The concentrate was subjected to distillation under reduced pressure, whereby 258.0 g of 3-chloro-1-thiocyanato-2-propene were obtained.

Yield: 84.1%

Purity: 98.1%

Boiling point: $83-88°$ C./5 mmHg $^1$H-NMR spectrum (CDCl$_3$) δ: 3.59(d,J=7.8Hz,(trans)), 3.80(d,J=7.0Hz,(cis)), 6.04(dt,J=7.0Hz,7.0Hz,(cis)), 6.06 (dt,J=14.0Hz,7.8Hz,(trans)), 6.39(d,J=14.0Hz,(trans)), 6.42 (d,J=7.0Hz,(cis)).

Example 2

In 250 ml of water, 200 g of sodium thiocyanate were dissolved. To the resulting solution, 250 g of 1,3-dichloropropene were added, followed by heating at $60°$ C. for 6 hours. The reaction mixture was cooled down to room temperature and poured in 200 ml of water, followed by extraction with 500 ml of xylene once. The organic layer was washed with 500 ml of saturated saline, dried over anhydrous sodium sulfate and then concentrated under reduced pressure. The concentrate was subjected to distillation under reduced pressure, whereby 241.8 g of 3-chloro-1-thiocyanato-2-propene were obtained.

Yield: 78.6%

Purity: 97.8%

Boiling point: $84-88°$ C./5 mmHg

Example 3

In 12 ml of acetonitrile, 2.14 g of sodium thiocyanate were dissolved. To the resulting solution, 2.66 g of 1,3-dichloropropene were added, followed by heating for 3 hours at the reflux temperature ($80-82°$ C.) of acetonitrile. The reaction mixture was cooled down to room temperature and acetonitrile was distilled off under reduced pressure. After the addition of 20 ml of water to the residue, the resulting mixture was extracted twice with 20 ml of ethyl acetate. The organic layer was washed with 20 ml of saturated saline, dried over anhydrous sodium sulfate and then concentrated under reduced pressure. The concentrate was then purified by distillation under reduced pressure, whereby 2.89 g of 3-chloro-1-thiocyanato-2-propene were obtained.

Yield: 88.4%

Purity: 98.1%

Boiling point: $83-88°$ C./5 mmHg

Example 4

In 12 ml of methanol, 2.14 g of sodium thiocyanate were dissolved. To the resulting solution, 2.66 g of 1,3- dichloropropene were added, followed by heating for 3 hours at the reflux temperature (64–66° C.) of methanol. The reaction mixture was cooled down to room temperature and methanol was distilled off under reduced pressure. After the addition of 20 ml of water to the residue, the resulting mixture was extracted twice with 20 ml of ethyl acetate. The organic layer was washed with 20 ml of saturated saline, dried over anhydrous sodium sulfate and then concentrated under reduced pressure. The concentrate was then purified by distillation under reduced pressure, whereby 2.86 g of 3-chloro-1-thiocyanato-2-propene were obtained.

Yield: 87.6%

Purity: 98.2%

Boiling Point: 84–88° C./5 mmHg

Example 5

In 12 ml of acetone, 2.14 g of sodium thiocyanate were dissolved. To the resulting solution, 2.66 g of 1,3-dichloropropene were added, followed by heating for 5 hours at the reflux temperature (55–58° C.) of acetone. The reaction mixture was cooled down to room temperature and acetone was distilled off under reduced pressure. After the addition of 20 ml of water to the residue, the resulting mixture was extracted twice with 20 ml of ethyl acetate. The organic layer was washed with 20 ml of saturated saline, dried over anhydrous sodium sulfate and then concentrated under reduced pressure. The concentrate was then purified by distillation under reduced pressure, whereby 2.72 g of 3-chloro-1-thiocyanato-2-propene were obtained.

Yield: 83.1%

Purity: 97.9%

Boiling point: 83–88° C./5 mmHg

Example 6

To 12 ml of diisopropyl ether, 2.14 g of sodium thiocyanate, 2.66 g of 1,3-dichloropropene and 33 mg of tetraethylammonium chloride were added. The resulting mixture was heated for 3 hours at the reflux temperature (68–70° C.) of diisopropyl ether. The reaction mixture was cooled down to room temperature and the salts so precipitated were filtered. The filtrate was washed with 20 ml of saturated saline, dried over anhydrous sodium sulfate and then concentrated under reduced pressure. The concentrate was then purified by distillation under reduced pressure, whereby 2.71 g of 3-chloro-1-thiocyanato-2-propene were obtained.

Yield: 82.7%

Purity: 97.9%

Boiling point: 83–88° C./5 mmHg

Example 7

To 20 ml of toluene, 2.14 g of sodium thiocyanate, 2.66 g of 1,3-dichloropropene and 43 mg of tetrabutyl ammonium chloride were added. The resulting mixture was heated for 5 hours at the reflux temperature (110–115° C.) of toluene. The reaction mixture was cooled down to room temperature, followed by the addition of 20 ml of water to dissolve the resulting salts therein. The organic layer was separated, washed with 20 ml of saturated saline, dried over anhydrous sodium sulfate and concentrated under reduced pressure. The concentrate was purified by distillation under reduced pressure, whereby 2.59 g of 3-chloro-1-thiocyanato-2-propene were obtained.

Yield: 78.6%

Purity: 97.4%

Boiling point: 83–88° C./5 mmHg

Example 8

To 20 ml of dimethyl sulfoxide, 2.14 g of sodium thiocyanate, 2.66 g of 1,3-dichloropropene and 43 mg of tetrabutylammonium chloride were added, followed by the reaction at 25–30° C. for 3 hours. To the reaction mixture, 100 ml of water and 100 ml of isopropyl ether were added and they were stirred. The reaction mixture was then allowed to stand to separate the organic layer. The organic layer so obtained was washed with 50 ml of saturated saline, dried over anhydrous sodium sulfate and concentrated under reduced pressure. The concentrate was then purified by distillation under reduced pressure, whereby 2.41 g of 3-chloro-1-thiocyanato-2-propene were obtained.

Yield: 73.0%

Purity: 97.2%

Boiling point: 83–88° C./5 mmHg

Comparative Example 1

To 12 ml of diisopropyl ether, 2.14 g of sodium thiocyanate and 2.66 g of 1,3-dichloropropene were added, followed by reaction for 7 hours at the reflux temperature (68–70° C.) of diisopropyl ether. The reaction hardly proceeded and only a trace amount of 3-chloro-1-thiocyanato-2-propene was obtained.

PROCESS 2

Example 9

A mixture of 198 g of 3-chloro-1-thiocyanato-2-propene, 1375 ml of xylene and 9.35 g of copper (II) chloride was heated for one hour at the reflux temperature of xylene. The reaction mixture was cooled down to room temperature and the copper salt was removed by filtration. The filtrate was concentrated under reduced pressure. The concentrate was subjected to distillation under reduced pressure, whereby 184.0 g of 3-chloro-1-isothiocyanato-1-propene were obtained.

Yield: 90.7%

Purity: 97.6%

Boiling point: 60–75° C./5 mmHg $^1$H-NMR spectrum (CDCl$_3$)δ: 4.06(d,J=5.7Hz,(trans)), 4.18(d,J=7.4Hz,(cis)), 5.60(dt,J=8.1Hz,5.7Hz,(cis)), 5.92 (dt,J=13.5Hz,7.4Hz,(trans)), 6.15(d,J=8.1Hz,(cis)), 6.27(d, J=13.5Hz,(trans)).

Example 10

A mixture of 1.34 g of 3-chloro-1-thiocyanato-2-propene, 5 ml of toluene and 0.20 g of copper (I) chloride was heated for 4 hours at the reflux temperature of toluene. The reaction mixture was cooled down to room temperature and the copper salt was removed by filtration. The filtrate was concentrated under reduced pressure. The concentrate was subjected to distillation under reduced pressure, whereby 1.23 g of 3-chloro-1-isothiocyanato-1-propene were obtained.

Yield: 90.0%

Purity: 98.0%

Boiling point: 62–75° C./5 mmHg

Example 11

A mixture of 6.70 g of 3-chloro-1-thiocyanato-2-propene, 25 ml of toluene and 0.33 g of magnesium chloride was heated at the reflux temperature of toluene for 4 hours. The reaction mixture was cooled down to room temperature and the magnesium salt was removed by filtration. The filtrate was concentrated under reduced pressure. The concentrate was subjected to distillation under reduced pressure, whereby 6.10 g of 3-chloro-1-isothiocyanato-1-propene were obtained.

Yield: 89.8%

Purity: 98.6%

Boiling point: 63–75° C./5 mmHg

Example 12

A mixture of 6.70 g of 3-chloro-1-thiocyanato-2-propene, 25 ml of toluene and 0.33 g of cobalt chloride was heated at the reflux temperature of toluene for 4 hours. The reaction mixture was cooled down to room temperature and the cobalt salt was removed by filtration. The filtrate was concentrated under reduced pressure. The concentrate was subjected to distillation under reduced pressure, whereby 5.96 g of 3-chloro-1-isothiocyanato-1-propene were obtained.

Yield: 87.6%

Purity: 98.5%

Boiling point: 62–75° C./5 mmHg

Comparative Example 2

A mixture of 1.34 g of 3-chloro-1-thiocyanato-2-propene and 5 ml of dioxane was heated at the reflux temperature of dioxane for 6 hours. The reaction mixture was cooled down to room temperature and concentrated under reduced pressure. The concentrate was subjected to distillation under reduced pressure, whereby 0.73 g of 3-chloro-1-isothiocyanato-1-propene was obtained.

Yield: 51.8%

Purity: 95.0%

Boiling point: 64–75° C./5 mmHg

PROCESS 3

Example 13

In a reaction vessel, 26.8 g of 3-chloro-1-isothiocyanato-1-propene (a 2:3 mixture of cis-form and trans form) and 30 ml of chloroform were charged, followed by cooling to 0° C. While the internal temperature was kept at 10° C. or lower, 28.0 g of sulfuryl chloride were added dropwise to the resulting mixture over one hour. After the completion of the dropwise addition, the temperature was increased up to 50–60° C. and heating was carried out at the same temperature for 3 hours. The reaction mixture was cooled down to room temperature and then poured into 350 ml of a 10% aqueous solution of sodium carbonate. Then, the resulting mixture was extracted with 100 ml of chloroform twice. The organic layer was washed twice with 100 ml of saturated saline and dried over anhydrous sodium sulfate. The solvent was then distilled off, whereby 35.2 g of the crude reaction product were obtained. The crude reaction product was purified by distillation under reduced pressure, whereby 24.9 g of 2-chloro-5-chloromethyl-1,3-thiazole were obtained.

Yield: 69.2%

Purity: 93.8%

Boiling point: 107–109° C./17 mmHg $^1$H-NMR spectrum (CDCl$_3$)δ: 4.72(s,2H), 7.50(s,1H).

Example 14

In a reaction vessel, 26.8 g of 3-chloro-1-isothiocyanato-1-propene (a 2:3 mixture of cis-form and trans-form) and 30 ml of chloroform were charged, followed by cooling to 0° C. While the internal temperature was kept at 10° C. or lower, chlorine gas was introduced into the reaction mixture over 1.5 hours. The chorine gas was used in an amount of 22.3 g. After the completion of the reaction was confirmed, bubbling of nitrogen gas was effected to remove the excess chlorine gas and hydrogen chloride gas. The reaction mixture was poured in 350 ml of a 10% aqueous solution of sodium carbonate, followed by extraction twice with 100 ml of chloroform. The organic layer was washed twice with 100 ml of saturated saline and dried over anhydrous sodium sulfate. The solvent was then distilled off, whereby 34.3 g of the crude reaction product were obtained. The crude reaction product so obtained was purified by distillation under reduced pressure, whereby 23.0 g of 2-chloro-5-chloromethyl-1,3-thiazole were obtained.

Yield: 62.4%

Purity: 91.6%

Boiling point: 109–111° C./18 mmHg

Example 15

In a reaction vessel, 26.8 g of 3-chloro-1-isothiocyanato-1-propene (a 4:1 mixture of cis-form and trans-form) were charged, followed by cooling to 0° C. While the internal temperature was kept at 10° C. or lower, 28.0 g of sulfuryl chloride were added dropwise over one hour. After the completion of the dropwise addition, the temperature was increased up to 80° C. and heating was carried out at the same temperature for one hour. After the reaction mixture was cooled down to room temperature, it was poured into 200 ml of a 10% aqueous solution of sodium carbonate. The resulting mixture was then extracted twice with 200 ml of ethyl acetate. The organic layer was washed once with 100 ml of saturated saline and dried over anhydrous sodium sulfate. The solvent was then distilled off, whereby 35.2 g of the crude reaction product were obtained. The crude reaction product so obtained was subjected to distillation under reduced pressure, whereby 16.5 g of 2-chloro-5-chloromethyl-1,3-thiazole were obtained.

Yield: 45.3%

Purity: 92.6%

Boiling point: 107–109° C./17 mmHg

Reference Example 1

In a fractionating column of 50 cm height, 184 g of 3-chloro-1-isothiocyanato-1-propene (a 2:3 mixture of cis-form and trans-form) were fractionated, whereby 93.8 g of trans-3-chloro-1-isothiocyanato-1-propene were obtained.

Recovery of trans-form: 85.0%

Purity of trans-form: 98.5%

Boiling point: 74–75° C./5 mmHg

Example 16

In a reaction vessel, 26.8 g of trans-3-chloro-1-isothiocyanato-1-propene were charged, followed by cooling to 0° C. While the internal temperature was kept at 10° C. or lower, 28.0 g of sulfuryl chloride were added dropwise over 1.5 hours. After the completion of the dropwise addition, the temperature was increased up to 80° C. and heating was carried out at the same temperature for one hour. The reaction mixture was cooled down to room temperature and then poured in 200 ml of a 10% aqueous solution of sodium bicarbonate. The resulting mixture was extracted twice with 200 ml of ethyl acetate. The organic layer was washed once with 100 ml of saturated saline, and then dried over anhydrous sodium sulfate. The solvent was distilled off, whereby 37.9 g of the crude reaction product were obtained. The crude reaction product was subjected to distillation under reduced pressure, whereby 31.8 g of 2-chloro-5-chloromethyl-1,3-thiazole were obtained.

Yield: 91.2%

Purity: 96.6%

Boiling point: 108–110° C./17 mmHg

PROCESS 4

Example 17

In a reaction vessel, 26.8 g of 3-chloro-1-isothiocyanato-1-propene (a 2:3 mixture of cis-form and trans-form) were charged, followed by cooling to 0° C. While the internal temperature was kept at 10° C. or lower, 28.0.g of sulfuryl chloride were added dropwise over 1 hour. After the completion of the dropwise addition, the temperature was increased up to 80° C. and the heating was carried out at the same temperature for one hour. The reaction mixture was then cooled down to room temperature and then poured in 200 ml of a 10% aqueous solution of sodium carbonate. The resulting mixture was extracted twice with 200 ml of ethyl acetate. The organic layer was washed once with 100 ml of saturated saline, and then dried over anhydrous sodium sulfate. The solvent was distilled off, followed by simple distillation, whereby 32.7 g of the crude 2-chloro-5-chloromethyl-1,3-thiazole were obtained.

Yield: 68.3%

Purity: 70.4%

Boiling point: 107–109° C./17 mmHg

Example 18

In 4 ml of hexane, 2.01 g of the crude 2-chloro-5-chloromethyl-1,3-thiazole obtained in Example 17 were dissolved, followed by stirring at −20° C. for 5 minutes, whereby a white solid was precipitated. The white solid so obtained was collected by filtration, whereby 1.34 g of 2-chloro-5-chloromethyl-1,3-thiazole (purity: 97.0%) were obtained.

Example 19

In 4 ml of heptane, 2.03 g of the crude 2-chloro-5-chloromethyl-1,3-thiazole obtained in Example 17 were dissolved, followed by stirring at −20° C. for 5 minutes, whereby a white solid was precipitated. The white solid so obtained was collected by filtration, whereby 1.28 g of 2-chloro-5-chloromethyl-1,3-thiazole (purity: 97.3%) were obtained.

Japanese Priority Application Nos. 33649/1996, 128694/1996, 128695/1996, 129781/1996, 205885/1996, 207045/1996 and 207046/1996 are incorporated herein by reference in their entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of 2-chloro-5-chloromethyl-1,3-thiazole, which comprises rearranging 3-chloro-1-thiocyanato-2-propene in the presence of a salt of one or more than one metal selected from the group consisting of metals belonging to Group 2A, Group 7A, Group 8 and Group 1B of the long-form periodic table to obtain 3-chloro-1-isothiocyanato-1-propene; and reacting the 3-chloro-1-isothiocyanato-1-propene with a chlorinating agent.

2. The process of claim 1, wherein the 3-chloro-1-isothiocyanato-1-propene is trans.

3. The process of claim 1, wherein the chlorinating agent is sulfuryl chloride.

4. The process of claim 1, wherein the metal is selected from the group consisting of magnesium, manganese, ruthenium, cobalt, nickel, palladium and copper.

5. The process of claim 1, wherein the metal is selected from the group consisting of magnesium, cobalt, nickel, palladium and copper.

6. The process of claim 1, wherein the salt is selected from the group consisting of magnesium chloride, magnesium bromide, manganese chloride, cobalt chloride, nickel chloride, palladium chloride, copper (I) chloride, copper (II) chloride, copper oxide and copper thiocyanate.

7. The process of claim 1, wherein the salt is selected from the group consisting of magnesium chloride, manganese chloride, cobalt chloride, copper (I) chloride and copper (II) chloride.

8. A process for the preparation of 3-chloro-1-isothiocyanato-1-propene, which comprises rearranging 3-chloro-1-thiocyanato-2-propene in the presence of a salt of one or more than one metal selected from the group consisting of metals belonging to Group 2A, Group 7A, Group 8 and Group 1B of the long-form periodic table.

9. The process of claim 8, wherein the metal is selected from the group consisting of magnesium, manganese, ruthenium, cobalt, nickel, palladium and copper.

10. The process of claim 8, wherein the metal is selected from the group consisting of magnesium, cobalt, nickel, palladium and copper.

11. The process of claim 8, wherein the salt is selected from the group consisting of magnesium chloride, magnesium bromide, manganese chloride, cobalt chloride, nickel chloride, palladium chloride, copper (I) chloride, copper (II) chloride, copper oxide and copper thiocyanate.

12. The process of claim 8, wherein the salt is selected from the group consisting of magnesium chloride, manganese chloride, cobalt chloride, copper (I) chloride and copper (II) chloride.

13. A process for the preparation of 2-chloro-5-chloromethyl-1,3-thiazole, which comprises reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst, to obtain 3-chloro-1-thiocyanato-2-propene; rearranging the 3-chloro-1-thiocyanato-2-propene in the presence of a salt of one or more than one metal selected from the group consisting of metals belonging to Group 2A, Group 7A, Group 8 and Group 1B of the long-form periodic table to obtain 3-chloro-1-isothiocyanato-1-propene; and reacting the 3-chloro-1-isothiocyanato-1-propene with a chlorinating agent.

14. The process according to claim 13, wherein the 3-chloro-1-isothiocyanato-1-propene is trans.

15. The process of claim 13, wherein the chlorinating agent is sulfuryl chloride.

16. The process of claim 13, wherein the metal is selected from the group consisting of magnesium, manganese, ruthenium, cobalt, nickel, palladium and copper.

17. The process of claim 13, wherein the metal is selected from the group consisting of magnesium, cobalt, nickel, palladium and copper.

18. The process of claim 13, wherein the salt is selected from the group consisting of magnesium chloride, magnesium bromide, manganese chloride, cobalt chloride, nickel chloride, palladium chloride, copper (I) chloride, copper (II) chloride, copper oxide and copper thiocyanate.

19. The process of claim 13, wherein the salt is selected from the group consisting of magnesium chloride, manganese chloride, cobalt chloride, copper (I) chloride and copper (II) chloride.

20. The process of claim 13, wherein the 1,3-dichloropropene and the thiocyanate salt are reacted in the presence of water.

21. The process of claim 20, wherein the 1,3-dichloropropene and the thiocyanate salt are reacted in the presence of a phase transfer catalyst.

22. The process of claim 13, wherein the 1,3-dichloropropene and the thiocyanate salt are reacted in the presence of an organic solvent which is water soluble and has a boiling point of 150° C. or lower.

23. The process of claim 13, wherein the 1,3-dichloropropene and the thiocyanate salt are reacted in an organic solvent in the presence of a phase transfer catalyst.

24. A process for the preparation of 3-chloro-1-isothiocyanato-1-propene, which comprises reacting 1,3-dichloropropene and a thiocyanate salt (a) in the presence of water, (b) in the presence of an organic solvent which is water-soluble and has a boiling point of 150° C. or lower, or (c) in an organic solvent in the presence of a phase transfer catalyst, to obtain 3-chloro-1-thiocyanato-2-propene; and rearranging the 3-chloro-1-thiocyanato-2-propene in the presence of a salt of one or more than one metal selected from the group consisting of metals belonging to Group 2A, Group 7A, Group 8 and Group 1B of the long-form periodic table.

25. The process of claim 24, wherein the metal is selected from the group consisting of magnesium, ruthenium, cobalt, nickel, palladium and copper.

26. The process of claim 24, wherein the metal is selected from the group consisting of magnesium, cobalt, nickel, palladium and copper.

27. The process of claim 24, wherein the salt is selected from the group consisting of magnesium chloride, magnesium bromide, manganese chloride, cobalt chloride, nickel chloride, palladium chloride, copper (I) chloride, copper (II) chloride, copper oxide and copper thiocyanate.

28. The process of claim 24, wherein the salt is selected from the group consisting of magnesium chloride, manganese chloride, cobalt chloride, copper (I) chloride and copper (II) chloride.

29. The process of claim 24, wherein the 1,3-dichloropropene and the thiocyanate salt are reacted in the presence of water.

30. The process of claim 29, wherein the 1,3-dichloropropene and the thiocyanate salt are reacted in the presence of a phase transfer catalyst.

31. The process of claim 24, wherein the 1,3-dichloropropene and the thiocyanate salt are reacted in the presence of an organic solvent which is water soluble and has a boiling point of 150° C. or lower.

32. The process of claim 24, wherein the 1,3-dichloropropene and the thiocyanate salt are reacted in an organic solvent in the presence of a phase transfer catalyst.

* * * * *